US00PP29132P3

(12) United States Plant Patent
Oostveen

(10) Patent No.: US PP29,132 P3
(45) Date of Patent: Mar. 20, 2018

(54) ***MANDEVILLA* PLANT NAMED 'BBYEL'**

(50) Latin Name: *Mandevilla sanderi*
Varietal Denomination: BBYEL

(71) Applicant: Cornelis A. Oostveen, De Kwakel (NL)

(72) Inventor: Cornelis A. Oostveen, De Kwakel (NL)

(73) Assignee: DeZonnebloem Breeding B.V., De Kwakel (NL)

( * ) Notice: Subject to any disclaimer, the term of this patent is extended or adjusted under 35 U.S.C. 154(b) by 22 days.

(21) Appl. No.: 14/999,796

(22) Filed: Jun. 28, 2016

(65) Prior Publication Data

US 2017/0374777 P1 Dec. 28, 2017

(51) Int. Cl.
*A01H 5/02* (2006.01)

(52) U.S. Cl.
USPC ..... Plt./232

(58) Field of Classification Search
USPC ..... Plt./232
See application file for complete search history.

(56) References Cited

PUBLICATIONS

UPOV hit on *Mandevilla* plant named 'BBYEL', QZ PBR 20161381, filed Jun. 8, 2016.*

* cited by examiner

*Primary Examiner* — Anne M Grunberg
(74) *Attorney, Agent, or Firm* — C. A. Whealy

(57) ABSTRACT

A new and distinct cultivar of *Mandevilla* plant named 'BBYEL', characterized by its upright and vining plant habit; moderately vigorous growth habit; freely branching habit; moderately glossy dark green-colored leaves; freely flowering habit; and bright yellow-colored flowers.

2 Drawing Sheets

Botanical designation: *Mandevilla sanderi.*
Cultivar denomination: 'BBYEL'.

BACKGROUND OF THE INVENTION

The present invention relates to a new and distinct cultivar of *Mandevilla* plant, botanically known as *Mandevilla sanderi* and hereinafter referred to by the name 'BBYEL'.

The new *Mandevilla* plant is a product of a planned breeding program conducted by the Inventor in De Kwakel, The Netherlands. The objective of the breeding program is to create vining *Mandevilla* plants with unique and attractive flowers.

The new *Mandevilla* plant originated from a cross-pollination conducted by the Inventor in De Kwakel, The Netherlands in May, 2013 of a proprietary selection of *Mandevilla sanderi* identified as code number BC13-324, not patented, as the female, or seed parent with a proprietary selection of *Mandevilla sanderi* identified as code number BC12-015, not patented, as the male, or pollen, parent. The new *Mandevilla* plant was discovered and selected by the Inventor as a single flowering plant from within the progeny of the stated cross-pollination in a controlled greenhouse environment in De Kwakel, The Netherlands in August, 2014.

Asexual reproduction of the new *Mandevilla* plant by cuttings in a controlled greenhouse environment in De Kwakel, The Netherlands, since October, 2014 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BBYEL'. These characteristics in combination distinguish 'BBYEL' as a new and distinct *Mandevilla* plant:

1. Upright and vining plant habit.
2. Moderately vigorous growth habit.
3. Freely branching habit.
4. Moderately glossy dark green-colored leaves.
5. Freely flowering habit.
6. Bright yellow-colored flowers.

Plants of the new *Mandevilla* can be compared to plants of the female parent selection. Plants of the new *Mandevilla* differ primarily from plants of the female parent selection in the following characteristics:

1. Leaves of plants of the new *Mandevilla* are smaller with more pointed apices than leaves of plants of the female parent selection.
2. Plants of the new *Mandevilla* and the female parent selection differ in flower color as plants of the female parent selection have pale yellow-colored flowers.

Plants of the new *Mandevilla* can be compared to plants of the male parent selection. Plants of the new *Mandevilla* differ primarily from plants of the male parent selection in the following characteristics:

1. Plants of the new *Mandevilla* are not as compact as plants of the male parent selection.
2. Plants of the new *Mandevilla* have smaller flowers than plants of the male parent selection.

3. Plants of the new *Mandevilla* and the male parent selection differ in flower color as plants of the male parent selection have pale yellow-colored flowers.

Plants of the new *Mandevilla* can be compared to plants of *Mandevilla sanderi* 'Lancalifornia', disclosed in U.S. Plant Pat. No. 24,074. In side-by-side comparisons, plants of the new *Mandevilla* differ primarily from plants 'Lancalifornia' in the following characteristics:

1. Plants of the new *Mandevilla* are upright and vining in plant habit whereas plants of 'Lancalifornia' are upright to outwardly spreading in plant habit.
2. Leaves of plants of the new *Mandevilla* are smaller with more pointed apices than leaves of plants of 'Lancalifornia'.
3. Plants of the new *Mandevilla* have smaller flowers than plants of 'Lancalifornia'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'BBYEL' grown in a container.

The photograph on the second sheet is a close-up view of a typical flower and flower buds of 'BBYEL'.

DETAILED BOTANICAL DESCRIPTION

The aforementioned photographs and following observations, measurements and values describe plants grown during the late spring and early summer in 17-cm containers in a glass-covered greenhouse in De Kwakel, The Netherlands and under cultural practices typical of *Mandevilla* commercial production. During the production of the plants, day temperatures ranged from 16° C. to 25° C. and night temperatures ranged from 16° C. to 20° C. Plants were ten months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'BBYEL'.

Parentage:

*Female, or seed, parent*.—Proprietary selection of *Mandevilla sanderi* identified as code number BC13-324, not patented.

*Male, or pollen, parent*.—Proprietary selection of *Mandevilla sanderi* identified as code number BC12-015, not patented.

Propagation:

*Type*.—By vegetative cuttings.

*Time to initiate roots, summer*.—About ten days at temperatures about 24° C.

*Time to initiate roots, winter*.—About 16 days at temperatures about 21° C.

*Time to produce a rooted young plant, summer*.—About five weeks at temperatures about 24° C.

*Time to produce a rooted young plant, winter*.—About six weeks at temperatures about 21° C.

*Root description*.—Medium in thickness, fibrous; typically white to light brown in color, actual color of the roots is dependent on substrate composition, water quality, fertilizers, substrate temperature and physiological age of roots.

*Rooting habit*.—Freely branching; dense.

Plant description:

*Plant and growth habit*.—Upright and vining plant habit; moderately vigorous growth habit.

*Plant height*.—About 53.1 cm.

*Plant diameter (spread)*.—About 32.8 cm.

*Lateral branch description*.—Branching habit: Freely branching habit with about six primary and about 15 secondary lateral branches developing per plant. Length: About 41.7 cm. Diameter: About 2 mm. Internode length. About 1.3 cm. Strength: Strong. Texture and luster: Smooth, glabrous; glossy; becoming woody with development. Color, developing: Close to 174A. Color, developed: Close to 143B; when woody, close to 197B and 197C.

Leaf description:

*Arrangement*.—Opposite, simple.

*Length*.—About 6 cm.

*Width*.—About 3.5 cm.

*Shape*.—Ovate.

*Apex*.—Apiculate to nearly aristate.

*Base*.—Cordate.

*Margin*.—Entire.

*Texture and luster, upper surface*.—Smooth, glabrous; moderately glossy.

*Texture and luster, lower surface*.—Smooth, glabrous; slightly to moderately glossy.

*Venation pattern*.—Pinnate.

*Color*.—Developing leaves, upper surface: Close to 143A. Developing leaves, lower surface: Close to between 144A and 146B. Full expanded leaves, upper surface: Darker than between 143A and 146A; venation, close to 144A. Fully expanded leaves, lower surface: Close to between 144A and 146B; venation, close to 144B.

*Petioles*.—Length: About 8 mm. Diameter: About 1.25 mm. Strength: Moderately strong. Texture and luster, upper and lower surfaces: Smooth, glabrous; matte. Color, upper surface: Close to N148A. Color, lower surface: Close to 144B.

Flower description:

*Flower type and flowering habit*.—Single salverform flowers arranged in axillary cymes; flowers star-shaped and face upright to outwardly; freely flowering habit with about 6 to 33 flowers developing per inflorescence and about 180 flowers developing per plant during the flowering season.

*Natural flowering season*.—Plants flower continuously from spring into the autumn in The Netherlands; plants begin flowering about 20 weeks after planting.

*Flower longevity on the plant*.—About four to five days; flowers not persistent.

*Fragrance*.—Faint; acidic-sweet and pleasant.

*Inflorescence height*.—About 10.3 cm.

*Inflorescence diameter*.—About 7.5 cm.

*Flower buds*.—Length: About 4.1 cm. Diameter: About 1 cm. Shape: Oblanceolate to narrowly oblanceolate. Texture and luster: Smooth, glabrous; slightly glossy. Color: Close to 10A and 11A; towards the apex, close to 1A and 1B; towards the base, close to 145A.

*Flowers*.—Appearance: Flared trumpet, corolla fused and five-parted. Diameter: About 6 cm. Depth (length): About 3.8 cm. Throat diameter: About 1.2 cm. Tube length: About 3.2 cm. Tube diameter, distally: About 1.3 cm.

*Corolla*.—Quantity and arrangement: Five petals arranged in a single whorl; proximal 60% portion of the petals are fused into a tube. Petal length: About 6 cm. Petal width: About 2.4 cm. Petal shape and appearance: Roughly spatulate. Petal apex: Rounded. Petal margin: Entire. Petal texture and luster, upper surface: Smooth, glabrous; slightly velvety; matte. Petal texture and luster, lower surface: Smooth, glabrous; slightly glossy. Throat and tube texture: Smooth, glabrous; slightly velvety. Color: Petal, when opening, upper surface: Close to 14B. Petal, when opening, lower surface: Close to 12A. Petal, fully opened, upper and lower surfaces: Close to 12A; venation, close to 12A; color does not change with development. Throat: Close to 13A; venation, close to 17A to 17C. Tube: Close to 150B; venation, close to 150B.

*Calyx*.—Quantity and arrangement: Five sepals arranged in a single whorl. Length: About 2 mm. Diameter: About 3 mm. Sepal length: About 2 mm. Sepal width: About 1.5 mm. Sepal shape: Roughly deltoid. Sepal apex: Acute. Sepal base: Broadly cuneate. Sepal margin: Entire. Sepal texture and luster, upper surface: Smooth, glabrous; glossy. Sepal texture and luster, lower surface: Smooth, glabrous; moderately glossy. Sepal color: When opening, upper surface: Close to 144A. When opening, lower surface: Close to 143B. Fully opened, upper surface: Close to 144A to 144B. Fully opened, lower surface: Close to 144A.

*Peduncles*.—Length: About 5.4 cm. Diameter: About 3 mm. Strength: Strong. Aspect: About 30° from lateral branch axis. Texture and luster: Smooth, glabrous; matte. Color: Close to 144A.

*Pedicels*.—Length: About 1.6 cm. Diameter: About 1.5 mm. Strength: Strong. Aspect: About 40° from peduncle axis. Texture and luster: Smooth, glabrous; moderately glossy. Color: Close to 144C.

*Reproductive organs*.—Stamens: Quantity and arrangement: Typically five; basifixed; anthers connivent. Filament length: About 1 mm. Filament color: Close to 160B. Anther size: About 1.25 mm by 6 mm. Anther shape: Narrowly oblong. Anther color: Close to 160D. Pollen amount: None observed. Pistils: Quantity: Typically one. Pistil length: About 1.7 cm. Style length: About 1.6 cm. Style color: Close to 154C. Stigma shape: Club-shaped. Stigma color: Close to 160C. Ovary color: Close to 144A.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to be suitable for USDA Hardiness Zones 9 to 13.

It is claimed:

1. A new and distinct *Mandevilla* plant named 'BBYEL' as illustrated and described.

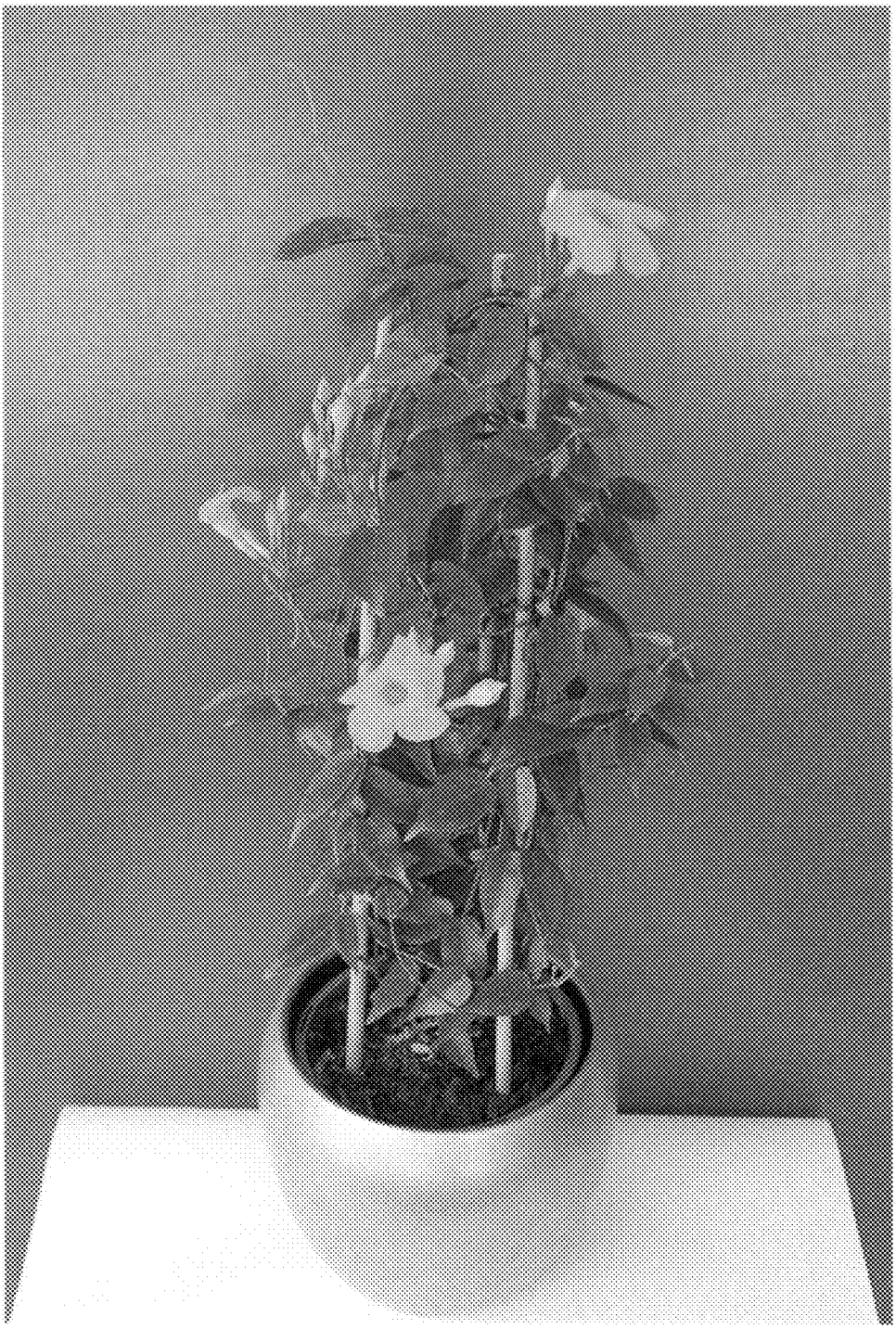

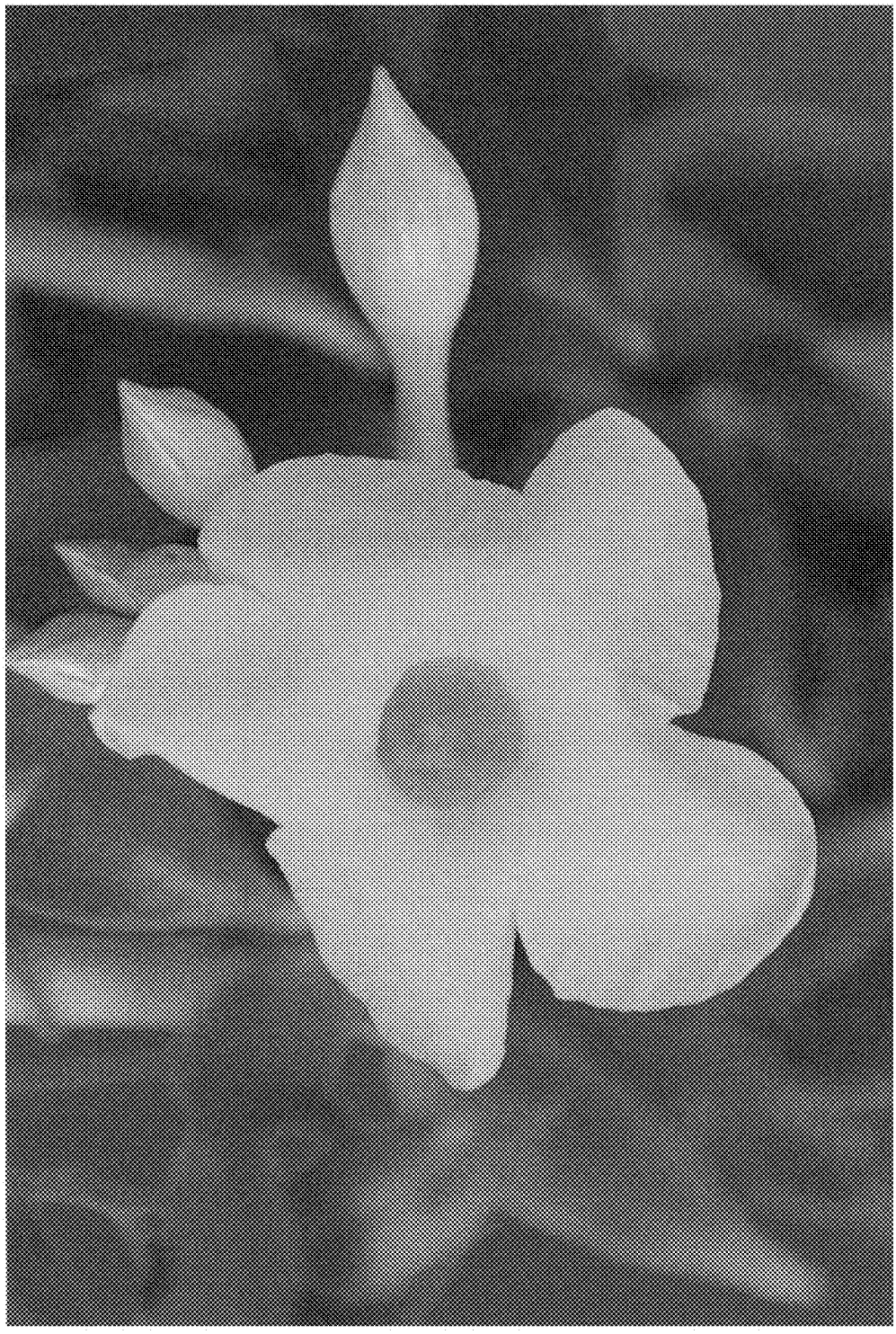

* * * * *